United States Patent
Barker et al.

(10) Patent No.: US 9,827,413 B2
(45) Date of Patent: Nov. 28, 2017

(54) LEAD CONSTRUCTION FOR DEEP BRAIN STIMULATION

(71) Applicant: BOSTON SCIENTIFIC NEUROMODULATION CORPORATION, Valencia, CA (US)

(72) Inventors: John Michael Barker, Ventura, CA (US); Anne Margaret Pianca, Santa Monica, CA (US); Geoffrey Abellana Villarta, Valencia, CA (US); Milad Girgis, North Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 404 days.

(21) Appl. No.: 13/864,030

(22) Filed: Apr. 16, 2013

(65) Prior Publication Data

US 2013/0274843 A1    Oct. 17, 2013

Related U.S. Application Data

(60) Provisional application No. 61/625,587, filed on Apr. 17, 2012.

(51) Int. Cl.
*A61N 1/05* (2006.01)

(52) U.S. Cl.
CPC .......... *A61N 1/0534* (2013.01); *A61N 1/0539* (2013.01)

(58) Field of Classification Search
CPC .................................................. A61N 1/0551
USPC ............................................. 607/116; 29/854
See application file for complete search history.

(56) References Cited

U.S. PATENT DOCUMENTS

| | | | | |
|---|---|---|---|---|
| 5,330,522 A | * | 7/1994 | Kreyenhagen | 607/122 |
| 5,554,176 A | * | 9/1996 | Maddison et al. | 607/9 |
| 5,584,873 A | * | 12/1996 | Shoberg et al. | 607/122 |
| 5,855,552 A | * | 1/1999 | Houser et al. | 600/374 |
| 5,865,843 A | * | 2/1999 | Baudino | 607/116 |
| 5,893,885 A | * | 4/1999 | Webster, Jr. | 607/122 |
| 6,181,969 B1 | | 1/2001 | Gord | |
| 6,181,971 B1 | * | 1/2001 | Doan | 607/116 |
| 6,304,784 B1 | * | 10/2001 | Allee et al. | 607/116 |

(Continued)

OTHER PUBLICATIONS

U.S. Appl. No. 12/177,823, filed Jul. 22, 2008.

(Continued)

*Primary Examiner* — Carl H Layno
*Assistant Examiner* — Erin M Piateski
(74) *Attorney, Agent, or Firm* — Lowe Graham Jones PLLC; Bruce E. Black

(57) ABSTRACT

A stimulation lead extends from a proximal end to a distal end and includes a plurality of electrodes disposed along the distal end of the lead; a plurality of terminals disposed along the proximal end of the lead; and an elongated body separating the plurality of electrodes from the plurality of terminals. The elongated body includes an outer tube of insulative material, and a cog-shaped conductor guide disposed within the outer tube. The conductor guide includes a central core and a plurality of protrusions extending outward from the central core. The plurality of protrusions and the outer tube define a plurality of pocket regions. The stimulation further includes a plurality of conductors disposed within the plurality of pocket regions, each conductor coupling at least one of the plurality of electrodes to at least one of the plurality of terminals.

13 Claims, 7 Drawing Sheets

(56) References Cited

U.S. PATENT DOCUMENTS

| | | | |
|---|---|---|---|
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,006,859 B1* | 2/2006 | Osorio et al. | 600/378 |
| 7,244,150 B1 | 7/2007 | Brase et al. | |
| 7,437,193 B2 | 10/2008 | Parramon et al. | |
| 7,450,997 B1 | 11/2008 | Pianca et al. | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,271,094 B1 | 9/2012 | Moffitt et al. | |
| 8,295,944 B2 | 10/2012 | Howard et al. | |
| 8,364,278 B2 | 1/2013 | Pianca et al. | |
| 8,391,985 B2 | 3/2013 | McDonald | |
| 2001/0018607 A1* | 8/2001 | Borgersen et al. | 607/121 |
| 2003/0204232 A1* | 10/2003 | Sommer et al. | 607/122 |
| 2004/0064024 A1* | 4/2004 | Sommer | 600/374 |
| 2004/0097965 A1* | 5/2004 | Gardeski et al. | 606/129 |
| 2005/0027342 A1* | 2/2005 | Shoberg et al. | 607/122 |
| 2005/0222659 A1* | 10/2005 | Olsen et al. | 607/116 |
| 2006/0089691 A1* | 4/2006 | Kaplan et al. | 607/116 |
| 2007/0150036 A1 | 6/2007 | Anderson | |
| 2007/0197892 A1* | 8/2007 | Shen et al. | 600/378 |
| 2007/0293922 A1* | 12/2007 | Soltis et al. | 607/122 |
| 2008/0004618 A1* | 1/2008 | Johnson et al. | 606/41 |
| 2009/0187222 A1 | 7/2009 | Barker | |
| 2009/0198312 A1* | 8/2009 | Barker | 607/116 |
| 2009/0222073 A1* | 9/2009 | Flowers et al. | 607/116 |
| 2009/0276021 A1 | 11/2009 | Meadows et al. | |
| 2010/0076535 A1 | 3/2010 | Pianca et al. | |
| 2010/0137928 A1* | 6/2010 | Duncan et al. | 607/5 |
| 2010/0268298 A1 | 10/2010 | Moffitt et al. | |
| 2010/0298761 A1* | 11/2010 | Staal et al. | 604/20 |
| 2010/0306997 A1* | 12/2010 | Pardo et al. | 29/825 |
| 2011/0004267 A1 | 1/2011 | Meadows | |
| 2011/0005069 A1 | 1/2011 | Pianca | |
| 2011/0078900 A1 | 4/2011 | Pianca et al. | |
| 2011/0130817 A1 | 6/2011 | Chen | |
| 2011/0130818 A1 | 6/2011 | Chen | |
| 2011/0196229 A1* | 8/2011 | Weiss et al. | 600/423 |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0232629 A1* | 9/2012 | Bloemer et al. | 607/116 |
| 2013/0030426 A1* | 1/2013 | Gallardo et al. | 606/33 |

OTHER PUBLICATIONS

U.S. Appl. No. 61/022,953, filed Jan. 23, 2008.
U.S. Appl. No. 61/170,037, filed Apr. 16, 2009.
U.S. Appl. No. 61/316,759, filed Mar. 23, 2010.
U.S. Appl. No. 61/494,247, filed Jun. 7, 2011.
U.S. Appl. No. 61/554,861, filed Nov. 2, 2011.
U.S. Appl. No. 61/591,046, filed Jan. 26, 2012.
U.S. Appl. No. 61/745,354, filed Dec. 21, 2012.
Official Communication for U.S. Appl. No. 13/864,049 dated Mar. 12, 2014.
Official Communication for U.S. Appl. No. 13/864,049 dated Aug. 6, 2014.
Official Communication for U.S. Appl. No. 13/864,049 dated Dec. 15, 2014.

\* cited by examiner

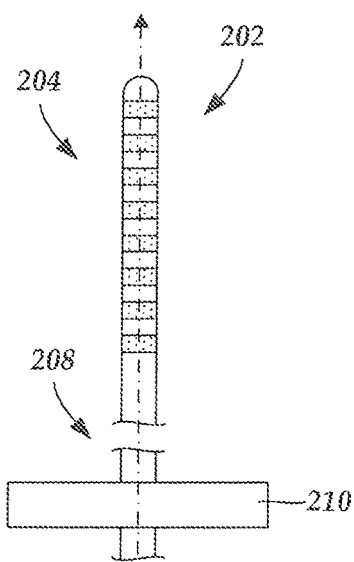
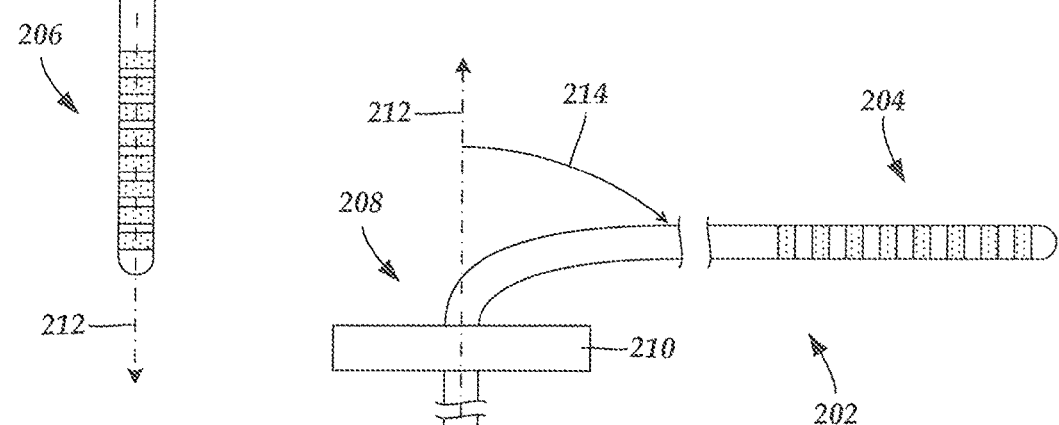
Fig. 2A
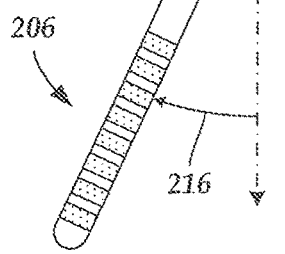
Fig. 2B

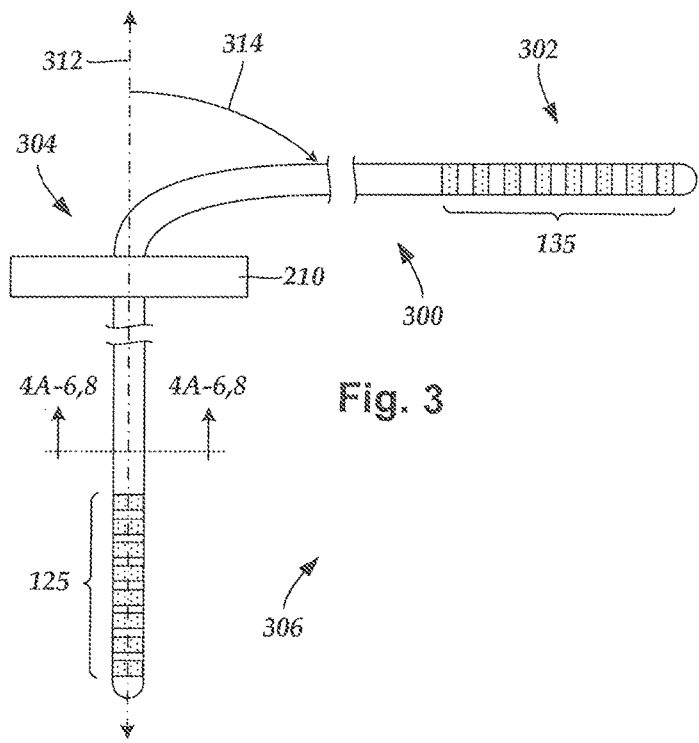
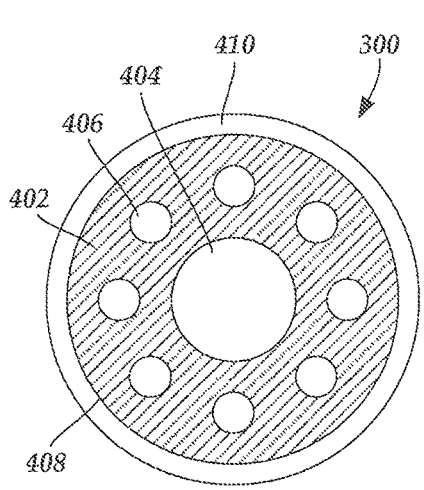
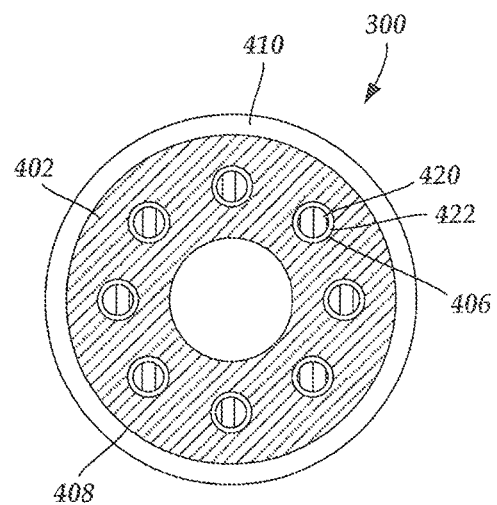

LEAD CONSTRUCTION FOR DEEP BRAIN STIMULATION

CROSS-REFERENCE TO RELATED APPLICATIONS

This application claims the benefit under 35 U.S.C. §119 (e) of U.S. Provisional Patent Application Ser. No. 61/625,587 filed on Apr. 17, 2012, which is incorporated herein by reference.

FIELD OF THE INVENTION

The present invention is directed to the area of implantable electrical stimulation systems and methods of making and using the systems. The present invention is also directed to implantable electrical stimulation leads with arrangements to facilitate lead straightness and compliance.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Conventionally, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by the electrode, typically in the form of a ring, disposed on the lead. The current projects from the electrode equally in every direction. Conventional deep brain stimulation leads may be unreliable and prone to failure. One study shows that lead breakage rates for some lead products are reported anywhere from 6.8-12.4%, and that the breakage occurs on average from 260-390 days. Thus in many cases, revision surgery is needed within a short period of time. This revision surgery is physically, mentally and financially taxing on the patient.

BRIEF SUMMARY

One embodiment is a stimulation lead extending from a proximal end to a distal end and including a plurality of electrodes disposed along the distal end of the lead; a plurality of terminals disposed along the proximal end of the lead; and an elongated body separating the plurality of electrodes from the plurality of terminals. The elongated body includes an outer tube of insulative material, and a cog-shaped conductor guide disposed within the outer tube. The conductor guide includes a central core and a plurality of protrusions extending outward from the central core. The plurality of protrusions and the outer tube define a plurality of pocket regions. The stimulation further includes a plurality of conductors disposed within the plurality of pocket regions, each conductor coupling at least one of the plurality of electrodes to at least one of the plurality of terminals.

Another embodiment is a stimulation lead extending from a proximal end to a distal end and including a plurality of electrodes disposed along the distal end of the lead; a plurality of terminals disposed along the proximal end of the lead; and an elongated body separating the plurality of electrodes from the plurality of terminals. The elongated body includes an outer tube of insulative material with at least one spiral incision formed along an outer surface thereof. The stimulation lead further includes a plurality of conductors disposed within the elongated body, each conductor coupling at least one of the plurality of electrodes to at least one of the plurality of terminals.

A further embodiment is a stimulation lead extending from a proximal end to a distal end and including a plurality of electrodes disposed along the distal end of the lead; a plurality of terminals disposed along the proximal end of the lead; and an elongated body separating the plurality of electrodes from the plurality of terminals. The elongated body includes an outer tube of insulative material, and a plurality of independent conductor tubes disposed within the outer tube. The stimulation lead further includes a plurality of conductors, each conductor disposed in a different one of the plurality of independent conductor tubes and each conductor coupling at least one of the plurality of electrodes to at least one of the plurality of terminals.

Yet another embodiment is a stimulation system that includes any of the stimulation leads described above and a control module configured and arranged to electrically couple to the stimulation lead. The control module includes a housing, an electronic sub-assembly disposed in the housing, and a connector for receiving the proximal end of the stimulation lead, the connector comprising a plurality of connector contacts configured to couple to at least one of the plurality of terminals disposed near the proximal end of the stimulation lead.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein:

FIG. 2A is a schematic side view of one embodiment of a intermediate portion of a lead being held in position by a retaining feature;

FIG. 2B is a schematic side view of one embodiment of a intermediate portion of the lead of FIG. 2A being held in position by the retaining feature of FIG. 2A and a proximal end of the lead being bent in a first direction, the bending of the proximal end causing a corresponding deflection of an opposing distal end of the lead in a second direction, opposite from the first direction;

FIG. 3 is a schematic side view of one embodiment of a intermediate portion of a lead held in position by the retaining feature of FIG. 2A and a proximal end of the lead being bent in a first direction, the bending of the proximal end not causing any corresponding deflections of an opposing distal end of the lead, according to the invention;

FIG. 4A is a transverse cross-sectional view of one embodiment of the lead of FIG. 3, the lead including a multi-lumen conductor guide that defines a central lumen and a plurality of conductor lumens arranged around the central lumen, according to the invention;

FIG. 4B is a transverse cross-sectional view of one embodiment of conductors disposed in each of a plurality of conductor lumens of the multi-lumen conductor guide of FIG. 4A such that a different single conductor is disposed in each of the conductor lumens, according to the invention;

Corresponding reference characters indicate corresponding components throughout the several views of the drawings.

DESCRIPTION OF THE EMBODIMENTS

The present invention is directed to the area of implantable electrical stimulation systems and methods of making and using the systems. The present invention is also directed to implantable electrical stimulation leads with arrangements to facilitate lead straightness and compliance.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Examples of deep brain stimulation devices and leads, as well as other leads and devices, can be found in, for example, U.S. Pat. Nos. 7,450,997; 7,783,359; 7,792,590; 7,809,446; 8,271,094; 8,295,944; and 8,391,985; U.S. Patent Applications Publication Nos. 2007/0150036; 2009/0187222; 2009/0276021; 2010/0076535; 2010/0268298; 2011/0004267; 2011/0005069; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; U.S. patent application Ser. No. 12/177,823; and U.S. Provisional Patent Application Ser. Nos. 61/170,037; 61/022,953; 61/316,759; 61/494,247; 61/554,861; and 61/591,046, all of which are incorporated herein by reference.

Figure 1:
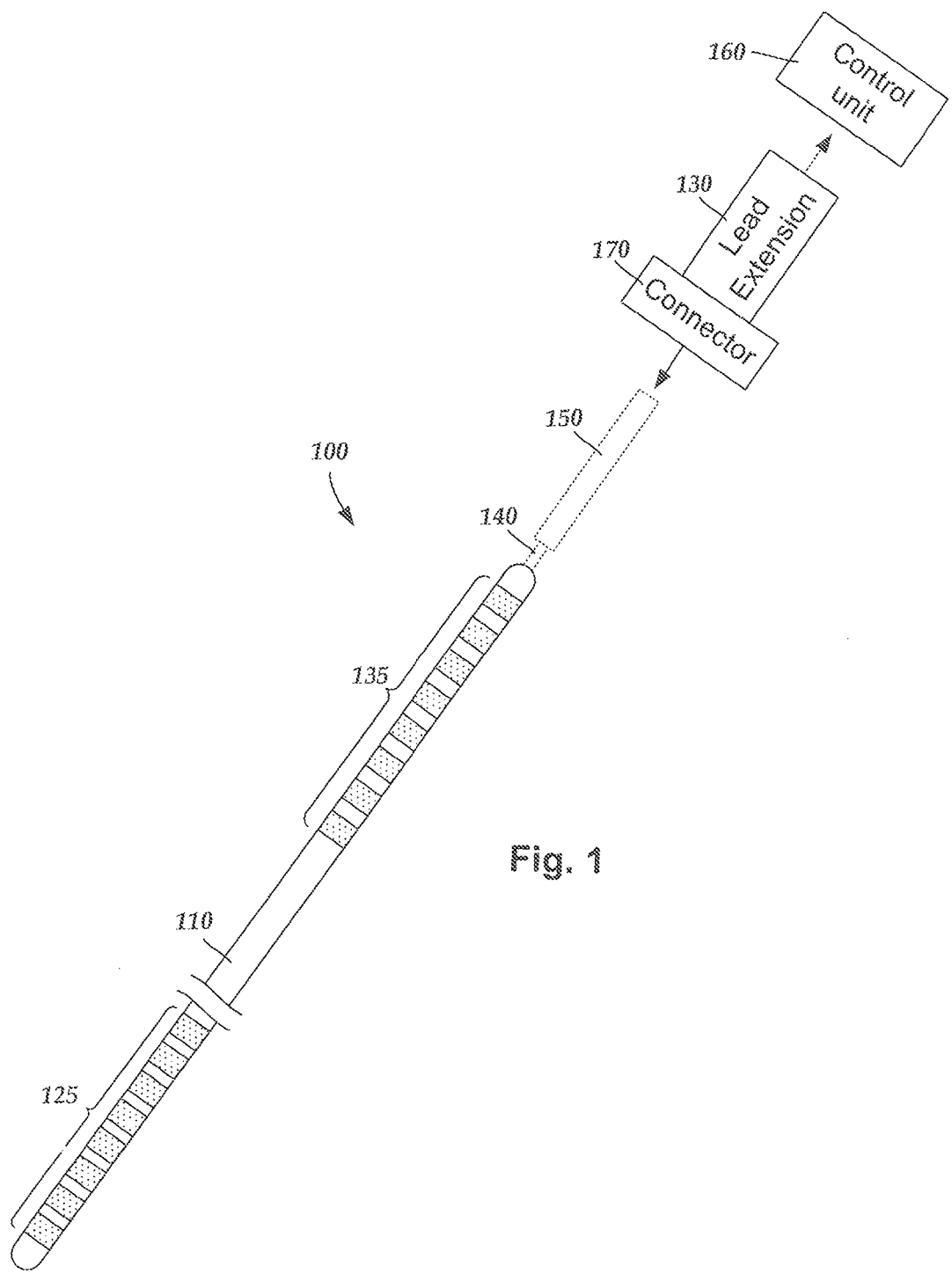
FIG. 1 is a schematic side view of one embodiment of a brain stimulation system that includes a lead, a lead extension, and a control unit, according to the invention.

FIG. 1 illustrates one embodiment of an electrical stimulation system 100 for brain stimulation. The electrical stimulation system 100 includes a lead 110, a plurality of electrodes 125 disposed at least partially about a circumference of the lead 110, a plurality of terminals 135, an optional lead extension 130 for connection of the electrodes 125 to a control unit 160, and a stylet 140 for assisting in insertion and positioning of the lead 110 in the patient's brain. It may be advantageous to include the lead extension 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140. Alternatively, the connector can be part of, or directly attached to, or temporarily attached to, the control unit.

The control unit 160 (or an external trial stimulator or temporary control unit) can be an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110. In some embodiments, the control unit may be an external or temporary control unit that is not implanted.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of 0.5 to 1.5 mm. In at least some embodiments, the lead 110 is rotatable so that the stimulation electrodes can be aligned with the target neurons after the neurons have been located using the recording electrodes. Stimulation electrodes may be disposed on the circumference of the lead 110 to stimulate the target neurons. Stimulation electrodes may be ring-shaped or segmented.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

It may be desirable for a lead to be flexible. As discussed above, during implantation a distal end of the lead is typically inserted into a burr hole in the patient's scalp and positioned such that the electrodes are disposed at a target stimulation location (e.g., the sub thalamic nucleus, the globus pallidus interna, the ventral intermediate nucleus, or the like). A proximal end of the lead is typically coupled to a connector of a lead extension or control unit. In which case, the lead may make an approximately 90° bend in proximity to an outer portion of the burr hole through which the distal end of the lead is extended. Consequently, it may be desirable for the lead to be flexible enough to be able to make such a bend.

Bending one portion of the lead, however, might cause a corresponding undesired deflection at another portion of the lead. For example, bending in a proximal portion or an intermediate portion of the lead may cause a corresponding undesired deflection at a distal end of the lead. Such a deflection may be caused, at least in part, by one or more conductors of the lead being held in tension, while one or more other conductors of the lead are held in compression. Deflection of the distal end of the lead could result in the loss of adequate stimulation, produce side effects, create a need for revision surgery, or cause injury to the patient.

FIG. 2A is a schematic side view of one embodiment of a lead 202 having a proximal portion 204, a distal portion 206, and an intermediate portion 208. The intermediate portion 208 of the lead 202 is held in position by a retaining feature 210 (e.g., a burr hole plug or cap, bone cement, one or more mini-plates, or the like). An axis 212 is shown passing through the portion of the lead 202 extending through the retaining feature 210. In FIG. 2A, the lead 202 is shown in a straight configuration, such that the entire lead 202 extends along the axis 212.

FIG. 2B is a schematic side view of one embodiment of the proximal portion 204 of the lead 202 bent in a first direction, away from the axis 212, as shown by arrow 214. As shown in FIG. 2B, bending of the proximal portion 204 of the lead 202 in a first direction causes a corresponding deflection of the distal portion 206 of the lead 202 in a second direction, away from the axis 212, as shown by arrow 216.

Accordingly, it is desirable for the lead to include one or more structural or material features that promote straightness and compliance of the lead or to reduce or prevent the bending of the lead proximal to a retaining feature (e.g., a burr hole plug or cap, bone cement, one or more mini-plates, or the like) from causing a corresponding deflection of the lead distal to the retaining feature.

Straightness can be reflected in at one or more aspects of the lead. For example, it is often desirable that a distal portion of the lead which extends beyond a delivery cannula during implantation of the lead remain straight so that the lead does not deviate from a straight trajectory during lead implantation. In at least some embodiments, the section of the lead that extends beyond the cannula has a length in the range of, for example, 15 to 40 mm. In addition, the straightness can be reflected by the ability of the lead to assume a straight configuration after being stored or packaged in a non-straight configuration. In particular, the lead preferably can be laid out straight without any bending (and without be further constrained) after being stored or packaged in a coiled arrangement for at least one month.

Compliance refers to the softness of the lead or the ability of the lead to deflect under its own mass. Preferably, the lead, in the absence of a stylet, is sufficiently soft to be readily deflected by application of a small force. Such a lead can reduce the possibility of damage to brain (or other) tissue after implantation of the lead as a result of movement of the tissue. The lead includes one or more features that promote straightness and compliance or which reduce, or even prevent, bending of a first portion of the lead from causing a corresponding deflection of a second portion of the lead or any combination of these desirable characteristics.

FIG. 3 is a schematic side view of one embodiment of a lead 300. The lead 300 has a proximal portion 302, an intermediate portion 304, and a distal portion 306. The intermediate portion 304 is held in a relatively stationary position by the retaining feature 210 (e.g., a burr hole plug or cap, bone cement, one or more mini-plates, or the like). An axis 312 is shown passing through the portion of the lead 300 extending through the retaining feature 210.

In FIG. 3, a portion of the lead 300 is shown bent in a first direction from the axis 312, as shown by arrow 314. It will be understood that the bend may occur at any suitable location along the length of the lead 300. For example, in some cases the bend may occur distal to the terminals and proximal to the electrodes. As shown in FIG. 3, bending of a portion of the lead 300 in a first direction does not cause a corresponding deflection of the distal portion 306 of the lead 300.

Turning to FIG. 4A, in at least some embodiments, the lead includes a lead body with an elongated multi-lumen conductor guide having multiple conductor lumens arranged about a central lumen. In at least some embodiments, the conductor lumens are arranged about the central lumen such that there are no other lumens extending along the multi-lumen conductor guide between the central lumen and each of the multiple conductor lumens. The conductor lumens include at least one helical section forming an enclosed pathway around at least a portion of the central lumen. In some embodiments, the conductor lumens are each configured and arranged to receive a single conductor. In other embodiments, at least one of the conductor lumens is configured and arranged to receive multiple conductors.

FIG. 4A is a transverse cross-sectional view of one embodiment of the lead 300. The lead 300 includes an elongated multi-lumen conductor guide 402. The multi-lumen conductor guide 402 may extend an entire longitudinal length of the lead 300 from the electrodes 125 to the terminals 135. As shown in FIG. 4A, the multi-lumen conductor guide 402 defines a central lumen 404 and a plurality of conductor lumens, such as conductor lumen 406. The conductor lumens can have any suitable cross-sectional shape (e.g., round, oval, rectangular, triangular, or the like).

In at least some embodiments, the plurality of conductor lumens 406 are encapsulated by the multi-lumen conductor guide 402 such that the conductor lumens 406 do not extend to an outer surface 408 of the multi-lumen conductor guide 402. In which case, when conductors (420 in FIG. 4B) are disposed in the conductor lumens 406, the conductors are not exposed along the outer surface 408 of the multi-lumen conductor guide 402. The central lumen 404 and the plurality of conductor lumens 406 can be arranged in any suitable manner. In preferred embodiments, the conductor lumens 406 are disposed in the multi-lumen conductor guide 402 such that the conductor lumens 406 are peripheral to the central lumen 404. In at least some embodiments, the lead 300 may include one or more outer coatings of material 410 disposed over the outer surface 408 of multi-lumen conductor guide 402.

The central lumen 404 may be configured and arranged to receive a stylet, such as the stylet 140 in FIG. 1. As discussed above, the stylet 140 can be used for assisting in insertion and positioning of the lead 300 in the patient's brain. The plurality of conductor lumens 406 are configured and arranged to receive conductors, which electrically couple the electrodes 125 to the terminals 135. FIG. 4B is a transverse cross-sectional view of one embodiment of conductors, such as conductor 420, disposed in the conductor lumens 406. In at least some embodiments, insulation 422 is disposed around the conductors 420 to prevent short-circuiting of the conductors 420.

Conventionally, a multi-lumen conductor guide is formed of a relatively stiff material, such as polyurethane. To promote compliance, a softer material (for example, a material of lower durometer than polyurethane) can be used for the multi-lumen conductor guide 402. Such materials include, for example, silicone or silicone-polyurethane copolymer. It will be recognized that the multi-lumen conductor guide need not have the specific form illustrated in FIGS. 4A and 4B and that other conductor guide arrangements can be used including arrangements that permit more than one conductor per lumen. In some embodiments, the conductor guide may be formed around the conductors by molding or other methods. In some embodiments, the conductor guide may be formed first and then the conductors inserted into the conductor guide.

Figure 5:
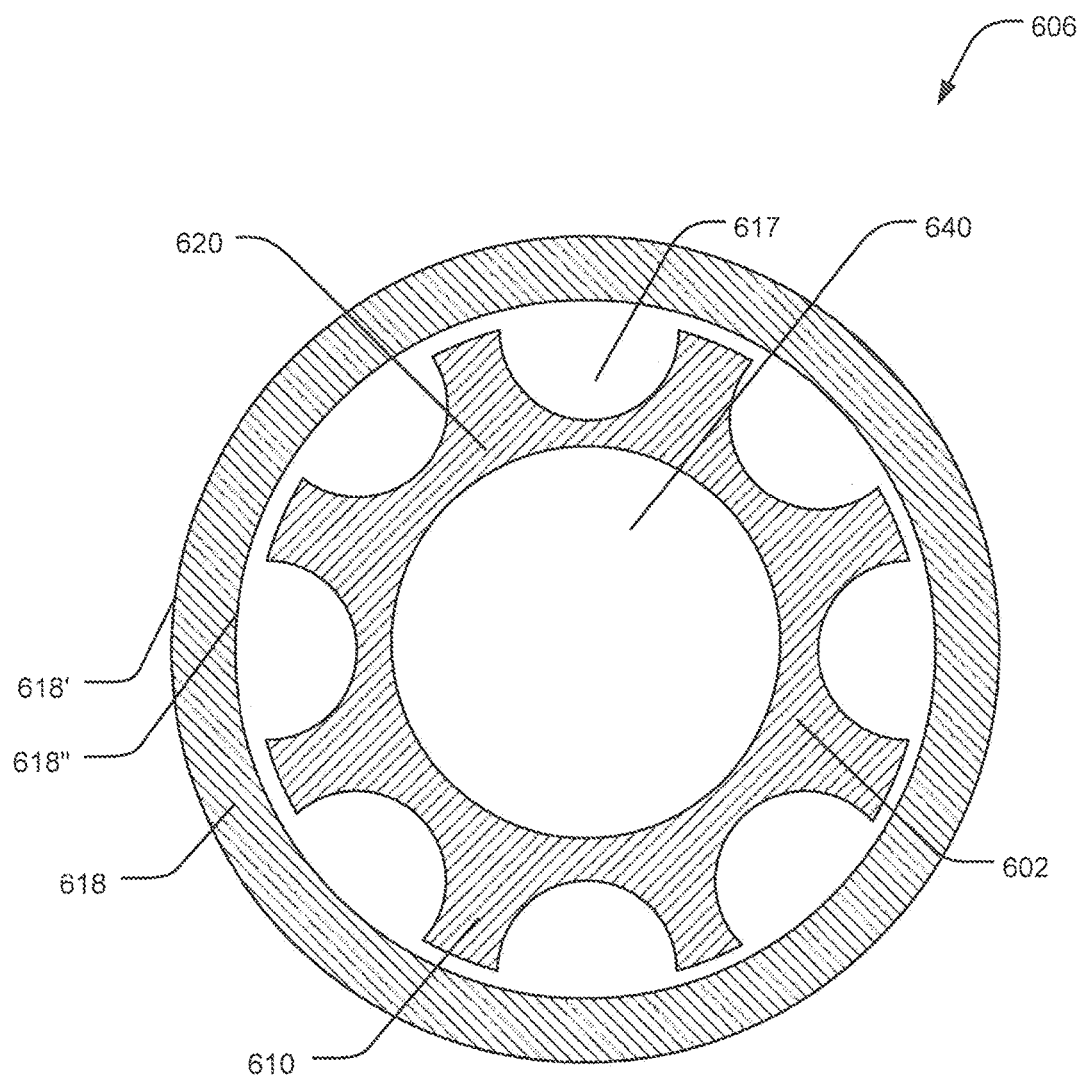
FIG. 5 is a schematic cross-sectional view of one embodiment of a stimulation lead with a cog-shaped conductor guide, according to the invention.

The shape of a conductor guide can be selected to improve lead straightness, lead compliance, or reduce deflection due to bending. FIG. 5 illustrates one embodiment of a lead 606 having a cog-shaped conductor guide 602 disposed within an outer tube 618. The outer tube 618 preferably includes an outer surface 618' and inner surface 618". The conductor guide 602 includes protrusions 610 extending outward from a core 620. The protrusions extend to the vicinity of the tube inner surface 618", and adjacent protrusions cooperate with the inner surface 618" of the outer tube 618 to define pocket regions 617. Conductors (not shown) are carried in the pocket regions. Those conductors can be single- or multifilar wires and can be solid or coiled. If desired a central lumen 640 can be provided in the center of the conductor guide 602, and a conductor can be carried there as well or the central lumen can be used to receive a stylet.

Figure 6:
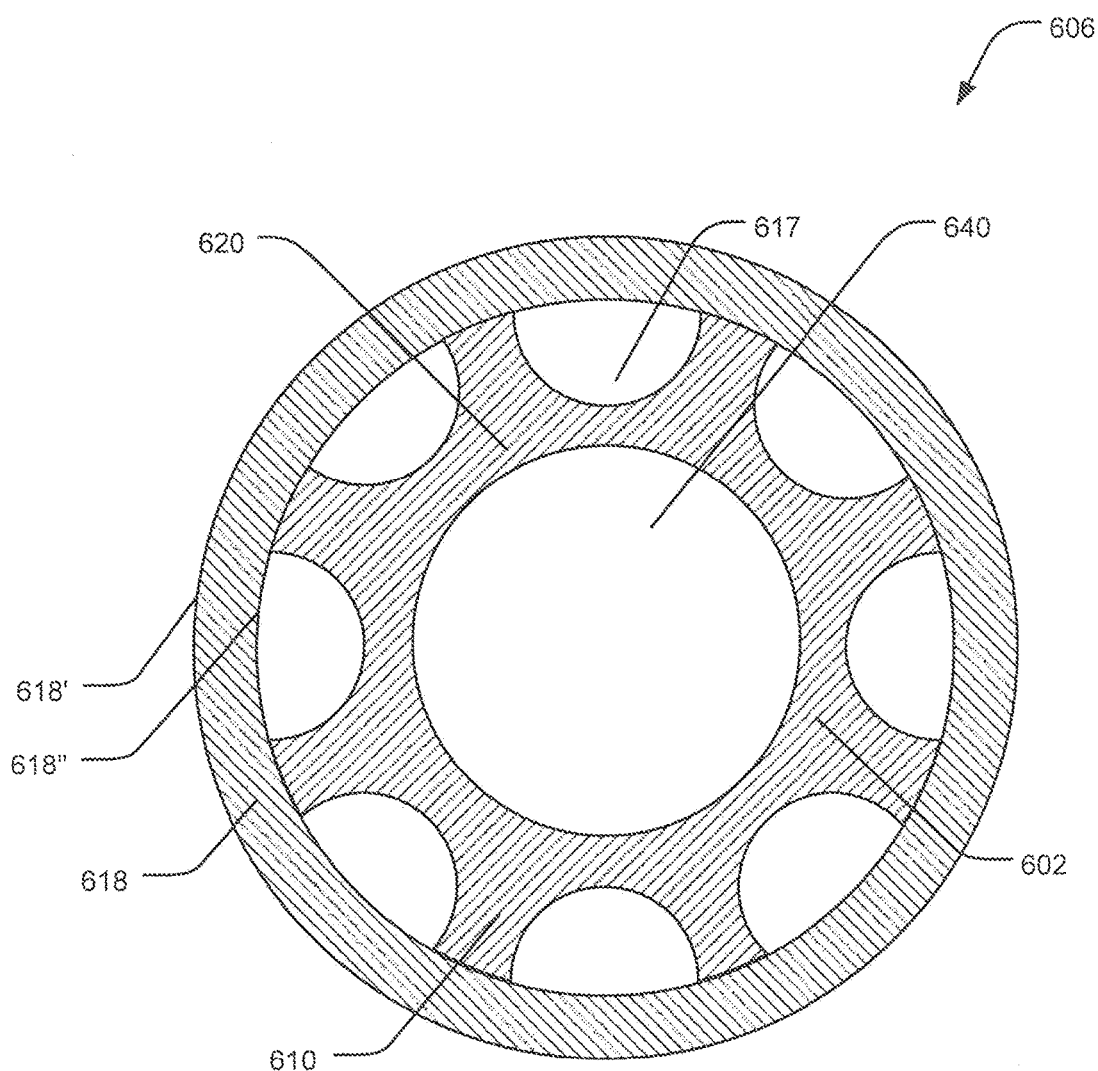
FIG. 6 is a schematic cross-sectional view of another embodiment of a stimulation lead with a cog-shaped conductor guide, according to the invention.

In at least some embodiments, the protrusions 610 are dimensioned with sufficient length to securely carry the conductors, without binding against inner surface 618" of outer tube 618. For example, an outer diameter of the conductor guide 602 (e.g., the outer diameter of the protrusions 610) is at least 5%, 10%, 15%, or 25% less than an inner diameter of the outer tube 618. As a result, conductors are not mechanically coupled. The freely-sliding conductor guide 602 allows for adequate spacing and bending of the lead 606. Alternatively, as illustrated in FIG. 6, the protrusions 610 may contact the inner surface 618" of the outer tube 618.

The pocket regions 617 may be equally spaced around the conductor guide 602 or they may be spaced in any regular or irregular arrangement. The pocket regions may be uniformly sized or may have different sizes. In at least some embodiments, the number of pocket regions equals the number of conductors. In other embodiments, the number of pocket regions may be more or fewer than the number of conductors; for example, the pocket regions may be sized to accommodate more than one conductor and, therefore, the conductor guide contains a smaller number of pocket regions than conductors.

The conductor guide 602 and outer tube 618 may be formed of any suitable material and they may be formed of the same or different materials. Suitable polymer materials include polyurethane, silicone, fluoropolymer, and copolymers thereof. In at least some embodiments, the conductor guide 602 is formed of a low durometer or soft material such as silicone or silicone-polyurethane co-polymer.

Figure 7:
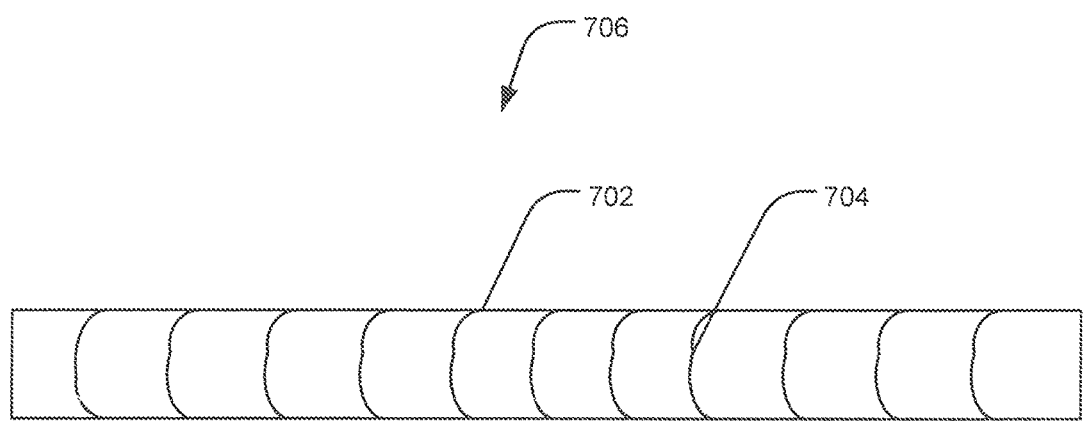
FIG. 7 is a schematic side view of one embodiment of a stimulation lead with a spiral cut along an outer body of insulation, according to the invention.

In accordance with at least some embodiment of the present disclosure, FIG. 7 shows a stimulation lead 706 having a spiral cut 704 along the outer insulation of the lead body 702. The spiral cut 704 can be made on the lead body 702 by any suitable process. In at least some embodiments, the spiral cut 704 is made using laser ablation, mechanical skiving, or machining. The spiral cut 704 on the lead body 702 minimizes cable coupling and provides improved lead straightness with increased lead compliance where needed. The spiral cut 704 also provides some relief from strain on the lead body 702. It will be understood that a spiral cut can be used in combination with any of the leads described herein.

Figure 8:
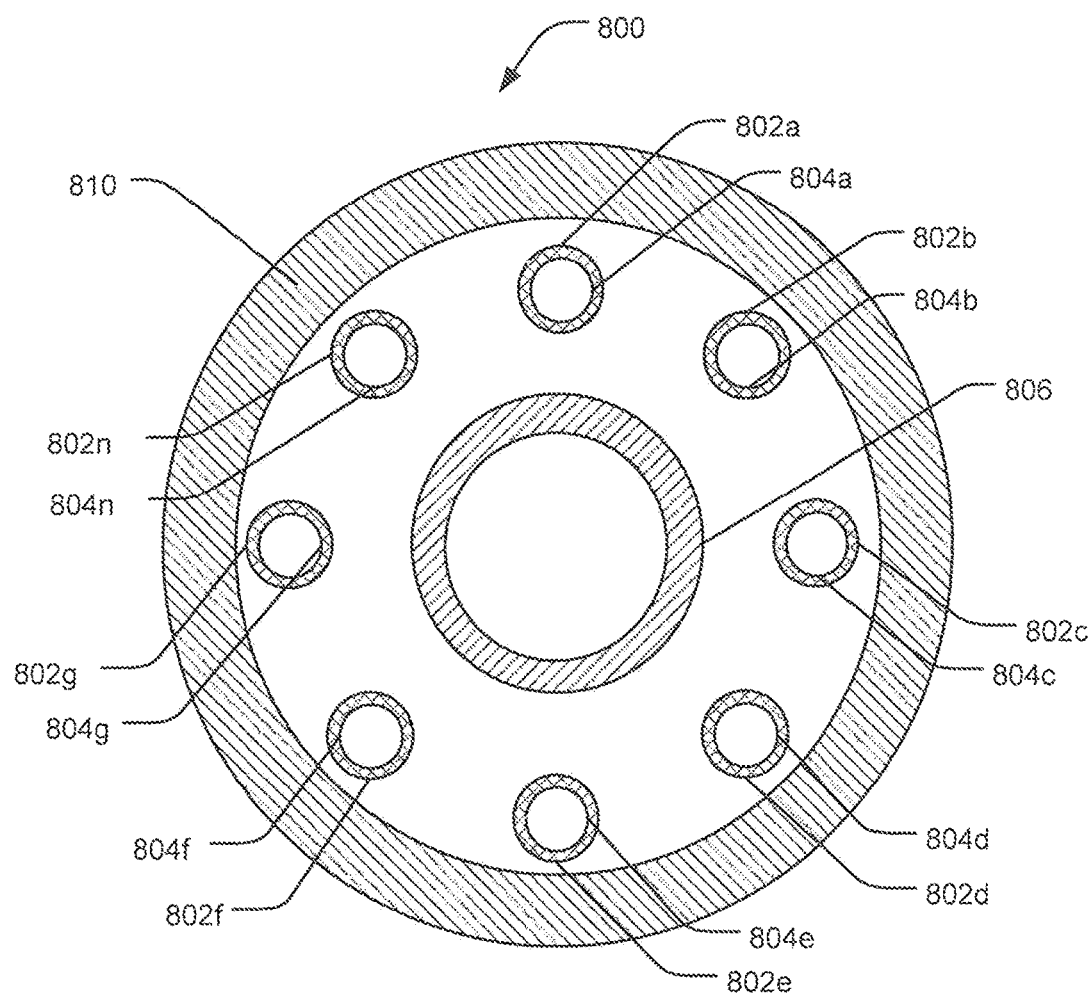
FIG. 8 is a schematic cross-sectional view of one embodiment of a stimulation lead with individual conductor tubes disposed in an outer tube, according to the invention.

In at least some embodiment of the present disclosure, one or more electrically isolated miniature coils are used as conductors, as shown in FIG. 8. In the illustrated embodiment, a stimulation lead 800 has an outer tube 810. Within that tube a number of independent conductor coils within tubes 802a-n are provided. Each independent tube carries a corresponding conductor coil 804a-n. The volume within the outer tube 810 and the aggregate volume of independent coils 804a-n are selected to provide sufficient spacing to preclude mechanical coupling among the independent tubes 802a-n. In some embodiments, a central tube 806 for receiving a stylet can be provided to assist in placement.

In some embodiments, further strain relief can be provided by providing conductors 804a-n as miniature coiled conductors, including coiled single- or multi-filar conductors. Use of such coiled conductors can reduce strain by providing inherent elasticity for each conductor 804a-n. Stress on a given conductor can be absorbed by stretching or compressing the coiled conductor.

The central tube 806, conductor tubes 802a-n, and outer tube 810 may be formed of any suitable material and they may be formed of the same or different materials. Suitable polymer materials include polyurethane, fluoropolymer, silicone, and copolymers thereof.

The leads described herein may be used in any medical or non-medical procedure, including any medical procedure where one or more body parts require electrical stimulation. In addition, at least certain aspects of the aforementioned embodiments may be combined with other aspects of the embodiments, or removed, without departing from the scope of the present disclosure.

While the present disclosure has been described by means of specific embodiments and applications thereof, numerous modifications and variations could be made thereto by those skilled in the art without departing from the scope of the present disclosure set forth in the following claims.

What is claimed as new and desired to be protected by United States Letters Patent is:

1. A stimulation lead extending from a proximal end to a distal end, the lead comprising:
   a plurality of electrodes disposed along the distal end of the lead;
   a plurality of terminals disposed along the proximal end of the lead;

an elongated body separating the plurality of electrodes from the plurality of terminals, the elongated body comprising
an outer tube of insulative material, and
a cog-shaped conductor guide disposed within, and separate from, the outer tube and extending from the proximal end of the lead to the distal end of the lead, the conductor guide comprising an outer surface, a central core, and a plurality of protrusions extending outward from the central core, wherein the plurality of protrusions and the outer tube define a plurality of pocket regions along the outer surface of the conductor guide with a one of the plurality of pocket regions defined between each pair of adjacent protrusions of the plurality of protrusions; and
a plurality of conductors disposed within the plurality of pocket regions with at least one conductor disposed in each of the plurality of pocket regions, each conductor coupling at least one of the plurality of electrodes to at least one of the plurality of terminals.

2. The stimulation lead of claim 1, wherein the conductor guide is made of silicone or a silicone-polyurethane copolymer.

3. The stimulation lead of claim 1, wherein the outer tube is made of silicone or a silicone-polyurethane copolymer.

4. The stimulation lead of claim 1, wherein the conductor guide further defines a central lumen.

5. The stimulation lead of claim 4, further comprising a stylet disposed within the central lumen.

6. The stimulation lead of claim 1, wherein the outer tube carries one or more spiral incisions formed on an outer surface of the outer tube.

7. The stimulation lead of claim 6, wherein the one or more spiral incisions extend from the proximal end of the lead to the distal end of the lead.

8. The stimulation lead of claim 7, wherein the one or more spiral incisions are formed by laser ablation, mechanical skiving, or machining.

9. A stimulation system, comprising:
the stimulation lead of claim 7; and
a control module configured and arranged to electrically couple to the stimulation lead, the control module comprising:
a housing,
an electronic subassembly disposed in the housing, and
a connector for receiving the proximal end of the stimulation lead, the connector comprising a plurality of connector contacts configured to couple to at least one of the plurality of terminals disposed near the proximal end of the stimulation lead.

10. The stimulation lead of claim 1, wherein an outer diameter of the conductor guide is at least 5% smaller than an inner diameter of the outer tube.

11. The stimulation lead of claim 1, wherein the conductor guide defines a number of the pocket regions equal to a number of the conductors.

12. The stimulation lead of claim 1, wherein the plurality of conductors are coiled conductors.

13. A stimulation system, comprising:
the stimulation lead of claim 1; and
a control module configured and arranged to electrically couple to the stimulation lead, the control module comprising:
a housing,
an electronic sub-assembly disposed in the housing, and
a connector for receiving the proximal end of the stimulation lead, the connector comprising a plurality of connector contacts configured to couple to at least one of the plurality of terminals disposed near the proximal end of the stimulation lead.

* * * * *